(12) United States Patent
Osborn, III (10) Patent No.: US 6,221,062 B1
(45) Date of Patent: *Apr. 24, 2001

(54) STRETCHABLE ABSORBENT STRUCTURE (75) Inventor: Thomas Ward Osborn, III, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/744,237

(22) Filed: Nov. 5, 1996

Related U.S. Application Data (63) Continuation of application No. 08/524,114, filed on Aug. 22, 1995, now abandoned, which is a continuation of application No. 08/337,901, filed on Nov. 10, 1994, now abandoned, which is a continuation of application No. 08/096,092, filed on Feb. 23, 1993, now abandoned.

(51) Int. Cl.[7] .................................................. A61F 13/15

(52) U.S. Cl. .................... 604/385.1; 604/387; 604/373; 604/385.2

(58) Field of Search ................................. 604/358, 365, 604/367–368, 372–373, 378, 385.1, 385.2, 387; 428/131, 138

(56) References Cited

U.S. PATENT DOCUMENTS

| | | | |
|---|---|---|---|
| 3,525,337 | * 8/1970 | Simmons et al. | 604/373 |
| 4,758,241 | * 7/1988 | Papajohn | 604/387 |
| 4,847,134 | * 7/1989 | Fahrenkrug et al. | 604/373 |
| 4,891,258 | * 1/1990 | Fahrenkrug | 604/373 |
| 4,950,264 | 8/1990 | Osborn, III . | |
| 5,007,906 | 4/1991 | Osborn, III et al. . | |
| 5,354,400 | 10/1994 | Lavash et al. . | |
| 5,451,219 | * 9/1995 | Suzuki et al. | 604/373 |
| 5,611,790 | 3/1997 | Osborn, III et al. . | |
| 5,658,269 | * 8/1997 | Osborn | 604/387 |
| 5,674,212 | * 10/1997 | Osborn | 604/387 |
| 5,683,375 | * 11/1997 | Osborn | 604/387 |
| 5,702,382 | * 12/1997 | Osborn | 604/387 |
| 5,704,930 | 1/1998 | Lavash et al. . | |
| 5,713,884 | * 2/1998 | Osborn | 604/387 |
| 5,824,004 | * 10/1998 | Osborn | 604/387 |
| 5,951,536 | 9/1999 | Osborn, III et al. . | |
| 6,059,764 | 5/2000 | Osborn, III et al. . | |

FOREIGN PATENT DOCUMENTS

| | | |
|---|---|---|
| 19998/83 | 4/1984 | (AU) . |
| 45217/85 | 2/1986 | (AU) . |
| 71912/91 | 8/1991 | (AU) . |

* cited by examiner

Primary Examiner—Mark O. Polutta
(74) Attorney, Agent, or Firm—Ingrid N. Hickman; Jeffrey V. Bamber (57) ABSTRACT

The present invention relates to a simple, cost-effective stretchable, superabsorbent material-containing absorbent structure that provides the superabsorbent material particles therein with improved liquid holding capacity. The stretchable absorbent structure can be used in absorbent articles such as diapers, sanitary napkins, panty liners, and incontinence pads. The stretchable absorbent structure comprises a stretchable absorbent liquid impervious barrier layer and a nonwoven component that is bonded to the barrier layer when the barrier layer is stretched at least partially toward its stretched condition, and superabsorbent, hydrogel-forming material deposited on or distributed within the nonwoven component.

13 Claims, 3 Drawing Sheets

Table 1... Typical Values for Stretch Parameters

| | LONGITUDINAL | | | WIDTH | | | FORCE WALL | |
|---|---|---|---|---|---|---|---|---|
| | % LONGITUDINAL STRETCH | g. OF FORCE TO EXTEND PAD | % PAD SET | % WIDTH STRETCH | g. OF FORCE TO EXTEND 1.0" STRIP | % PAD SET | % STRETCH | g. FORCE |
| CONDITIONS FOR STRETCH | 40% | ≤1000 g.<br>≤800 g. | ≤10<br>≤10<br>≤25 | 40% | ≤500 g.<br>≤400 g. | ≤10<br>≤25 | 50% | 1500 g.<br>2000 g.<br>2500 g. |
| | 25% | ≤800 g.<br>≤400 g.<br>≤300 g. | ≤10<br>≤25 | 25% | ≤500 g.<br>≤400 g. | ≤10<br>≤25 | 40% | 1500 g.<br>2000 g.<br>2500 g. |
| | | | | | | | 25% | 1500 g.<br>2000 g.<br>2500 g. |
| MINIMUM FORCE TO STRETCH | 25% | ≥50 g. | | | | | | |

Fig. 5

STRETCHABLE ABSORBENT STRUCTURE

This is a continuation of application Ser. No. 08/524,114, filed on Aug. 22, 1995, abandoned, which was a continuation of application Ser. No. 08/337, 901, filed on Nov. 10, 1994 (now abandoned), which was a continuation of application Ser. No. 08/096,092, filed Jul. 23, 1993, now abandoned.

FIELD OF THE INVENTION

The present invention relates to absorbent articles such as diapers, sanitary napkins, panty liners, and incontinence pads. More particularly, the present invention relates to a simple, cost-effective, stretchable, superabsorbent material-containing absorbent structure for absorbent articles, such as sanitary napkins and light incontinence products, that provides the superabsorbent material particles therein with improved liquid holding capacity.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Typically, most of the disposable absorbent articles of the types mentioned above are made of materials that will not stretch. That is, the materials (and the article itself) will not stretch under the forces that the absorbent article is normally subjected to when worn.

The Kimberly-Clark Corporation received a patent, U.S. Pat. No. 4,891,258, on a stretchable absorbent composite which issued to Fahrenkrug on Jan. 2, 1990. This patent is directed to a composite structure that is comprised of at least four layers: a liquid-pervious layer, a liquid-impervious layer, an absorbent layer, and a stretchable layer. The stretchable layer can comprise an impervious elastomeric film that is apertured and placed between the liquid-pervious layer and the absorbent layer. The stretchable layer is stretch-bonded to the other layers and, upon relaxing the stretched layer, a plurality of rugosities are formed in the liquid-pervious layer, liquid-impervious layer, and absorbent layer. The Fahrenkrug patent does not state what type of article for which the stretchable absorbent composite described therein might be useful. (The Applicants, therefore, do not concede that the stretchable absorbent composite is related to the same types of articles described herein.) The absorbent composite disclosed in the Fahrenkrug patent also suffers from a number of drawbacks. The Fahrenkrug patent requires the use of a separate stretchable layer which makes the stretchable absorbent composite stretchable, but appears to serve no purpose associated with the absorbency or liquid retention of the composite, adding to the cost of the same. In addition, because the stretchable layer is comprised of liquid impervious material, and is placed between the liquid-pervious layer and the absorbent layer, it presents an awkward structure which could interfere with the transmission of liquids to the absorbent layer.

A number of efforts by the Procter & Gamble Company, assignee of the present invention, have been directed to providing absorbent articles, such as sanitary napkins, panty liners, and incontinence pads, with an overall extensibility. Sanitary napkins and other absorbent articles comprised of most or all extensible components, which are provided with a degree of overall extensibility (which is preferably on the order of about 10% to 40%) are described in U.S. patent application Ser. No. 07/915,133 entitled "Stretchable Absorbent Articles" and Ser. No. 07/915,284 entitled "Extensible Absorbent Articles", both filed in the name of Osborn, et al. on Jul. 23, 1992 (PCT Publication Nos. WO 93/01785 and WO 93/01786, both published Feb. 4, 1993) (of which the present application is a continuation-in-part).

The absorbent articles described in the patent applications filed by Applicant's assignee work quite well. There are, however, some aspects of the absorbent articles that are described in these patent applications that can be improved. For example, the materials and manufacturing operations associated with making such absorbent articles extensible can result in such absorbent articles being substantially more expensive to produce than disposable absorbent articles currently on the market. It is, therefore, desirable to provide extensible absorbent structures, for absorbent articles that perform at least as well as the absorbent articles described in the above references, but which have fewer layers, and simpler constructions, and are, as a result, less expensive to manufacture. Therefore, the search for improved, as well as alternative, extensible absorbent articles to those described in the above patent applications has continued.

Thus, a need exists for an extensible absorbent article, such as a sanitary napkin, that is provided with an overall extensibility. In particular, a need exists for such absorbent articles that have fewer layers and simpler constructions, and are less expensive to manufacture than the absorbent articles described in the above references.

It is, therefore, an object of the present invention to provide an absorbent article, such as a sanitary napkin, that is provided with an overall extensibility which is preferably on the order of about 10% to 40%.

It is another object of the present invention to provide an alternative type of absorbent article, such as a sanitary napkin, that has fewer layers and a simpler construction that the extensible absorbent articles described in the above references.

It is still another object of the present invention to provide a superabsorbent material-containing absorbent article, such as a sanitary napkin, that provides the superabsorbent material particles therein with improved liquid holding capacity.

These and other objects of the present invention will be more readily apparent when considered in reference to the following description and when taken in conjunction with the accompanying drawings.

SUMMARY OF THE INVENTION

The present invention provides a stretchable absorbent structure for an absorbent article, such as a diaper, sanitary napkin, panty liner, or incontinence pad.

The stretchable absorbent structure comprises an absorbent component, such as a nonwoven web, that is laminated to a stretchable liquid impervious component that also serves as a barrier film. The nonwoven web is laminated to the barrier film when the barrier film is in an extended condition. The stretchable barrier film is then relaxed which provides a plurality of rugosities in the nonwoven web. The nonwoven material preferably has a plurality of superabsorbent material particles affixed thereto or distributed therein. The stretchable absorbent structure may be used as is, or the nonwoven side of the structure may be covered with a liquid pervious topsheet or by a superabsorbent material containment layer and then a topsheet.

The stretchable absorbent structure of the present invention provides a simple, cost-effective, stretchable, superabsorbent material-containing absorbent structure for absorbent articles, such as sanitary napkins and light incontinence products, that provides the superabsorbent material particles therein with improved liquid holding capacity.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
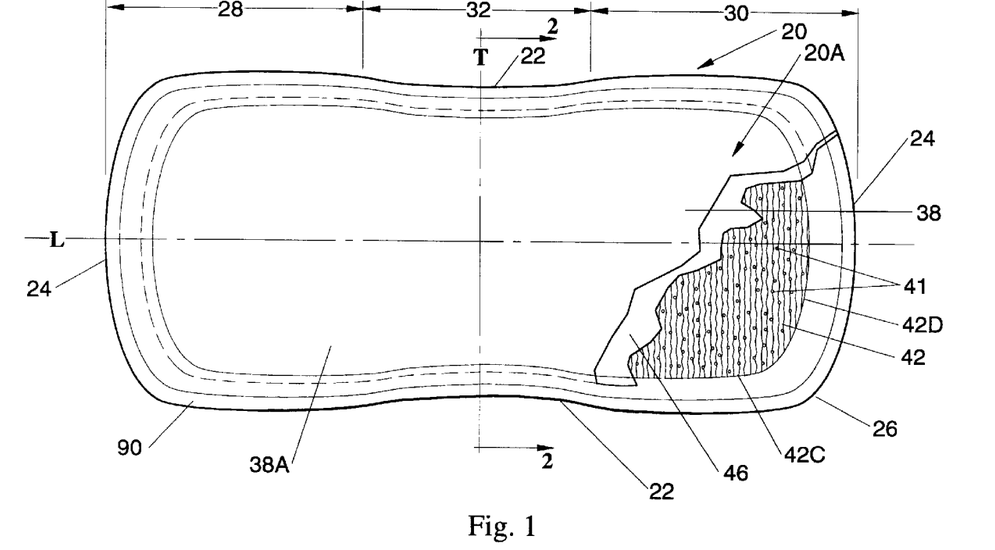
FIG. 1 is a top plan view of the stretchable absorbent structure of the present invention in a preferred sanitary napkin embodiment with a portion of the topsheet cut away to show the underlying structure.
Figure 2:
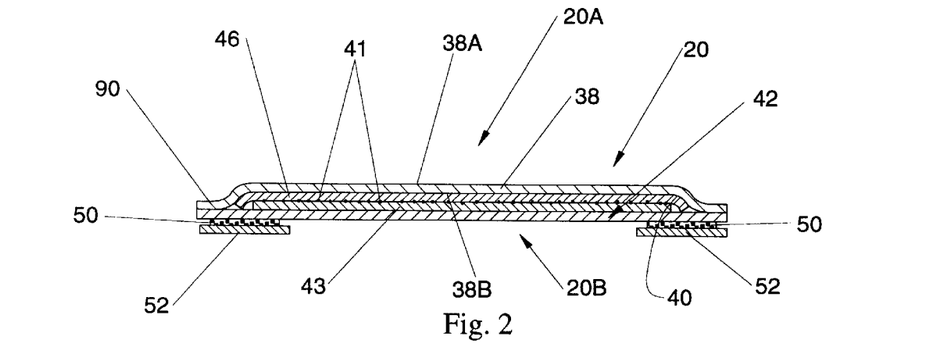
FIG. 2 is a cross sectional view of the sanitary napkin shown in FIG. 1 taken along line 2—2 of FIG. 1.

FIGS. 1 and 2 show the absorbent structure of the present invention in a preferred embodiment of a disposable absorbent article. The absorbent structure is an extensible, preferably stretchable, more preferably elastically extensible, three-dimensional superabsorbent material-containing absorbent structure. The absorbent article shown in FIGS. 1 and 2 in a preferred embodiment of an absorbent article, sanitary napkin 20.

The term "sanitary napkin", as used herein, refers to an article which is worn by females adjacent to the pudendal region that is intended to absorb and contain the various exudates which are discharged from the body (e.g., blood, menses, and urine). It should be understood, however, that the stretchable absorbent structure of the present invention can also be used with other feminine hygiene or catamenial pads such as panty liners, or other absorbent articles such as diapers, incontinence pads, and the like.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 is on the opposite side and is intended to be placed adjacent to the wearer's undergarments when the sanitary napkin 20 is worn.

The sanitary napkin 20 has two centerlines, a longitudinal center L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction. FIG. 1 shows that the sanitary napkin 20 also has two spaced apart longitudinal edges 22 and two spaced apart transverse or end edges (or "ends") 24, which together form the periphery 26 of the sanitary napkin 20.

The sanitary napkin 20 can be of any thickness, including relatively thick, relatively thin, or even very thin. The embodiment of the sanitary napkin 20 shown in FIG. 1 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 preferably has a caliper of less than about 3 millimeters. The thin sanitary napkin 20 shown should also be preferably relatively flexible, so that it is comfortable for the wearer. Examples of ultra-thin sanitary napkins are described in U.S. Pat. Nos. 4,950,264 and 5,009,653 issued to Osborn on Aug. 21, 1990, and Apr. 23, 1991, respectively.

FIG. 2 shows the individual components of the sanitary napkin 20 of the present invention. The sanitary napkin 20 shown in FIG. 2 comprises a liquid pervious topsheet 38, the absorbent structure 42 underlying the topsheet 38, and a superabsorbent material containment layer 46 positioned between the topsheet and the absorbent structure 42. The topsheet and superabsorbent material containment layer may be chosen from components described in PCT Publication Nos. WO 93/01785 and 93/01786. The sanitary napkin may, thus, be comprised of one or more extensible components in addition to the absorbent structure, and more preferably, is comprised of all extensible components, and has an overall extensibility.

Figure 4:
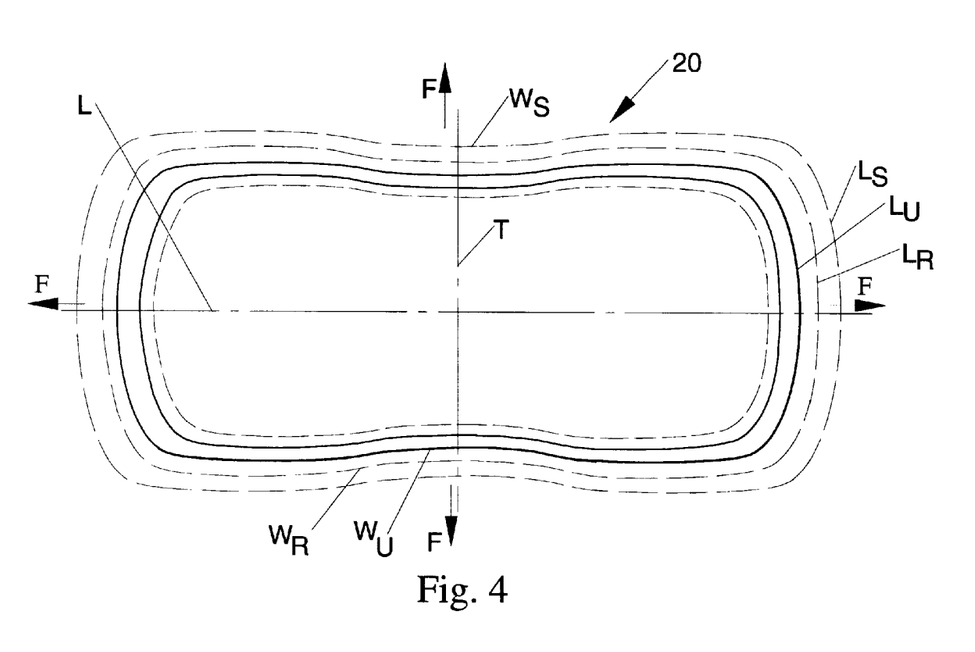
FIG. 4 is a top plan view showing the extensibility of the sanitary napkin.

The extensibility of the sanitary napkin 20 is shown in a simplified fashion in FIG. 4. The term "extensible", as used herein refers to articles that can increase in at least one of their dimensions in the x-y plane. The x-y plane is a plane generally parallel to the faces of the sanitary napkin 20. The term extensible includes articles that are stretchable and elastically stretchable (defined below). The sanitary napkin 20 shown in FIG. 4 is preferably extensible both in length and width. The sanitary napkin 20, in other embodiments however, may only be extensible in one of these directions. Preferably, the sanitary napkin 20 is extensible at least in the longitudinal direction.

The sanitary napkin 20 may in some preferred embodiments, in addition to being extensible, also be stretchable. The term "stretchable", as used herein, refers to articles that are extensible when stretching forces are applied to the article and offer some resistance to stretching. More preferably still, the sanitary napkin 20 may be elastically stretchable. The terms "elastically stretchable" or "elastically extensible" are intended to be synonomous. These terms, as used herein, mean that when the stretching forces are removed, the sanitary napkin will tend to return toward its unextended or unstretched (or "original") dimensions. The sanitary napkin 20 need not return all the way to its unstretched dimensions, however. It may, as shown in FIG. 4, return to relaxed dimensions (such as $L_R$ and $W_R$) between its unstretched dimensions and extended (or stretched dimensions) $L_S$ and $W_S$. Making the sanitary napkin elastically stretchable will reduce the undesirable tendency of the sanitary napkin to gather longitudinally inward (i.e., bunch longitudinally) when forces which tend to stretch the sanitary napkin are removed. This is particularly true when the wearer's panties contract.

The sanitary napkin 20 and the absorbent structure are preferably made extensible without attaching separate elastic strands in an extensible condition to either the sanitary napkin or the absorbent structure. The sanitary napkin and the absorbent structure can, thus, be said to be "non-elasticated" or "non-elasticized". However, the sanitary napkin and the absorbent structure are not precluded from having optional elastic strands.

Figure 5:
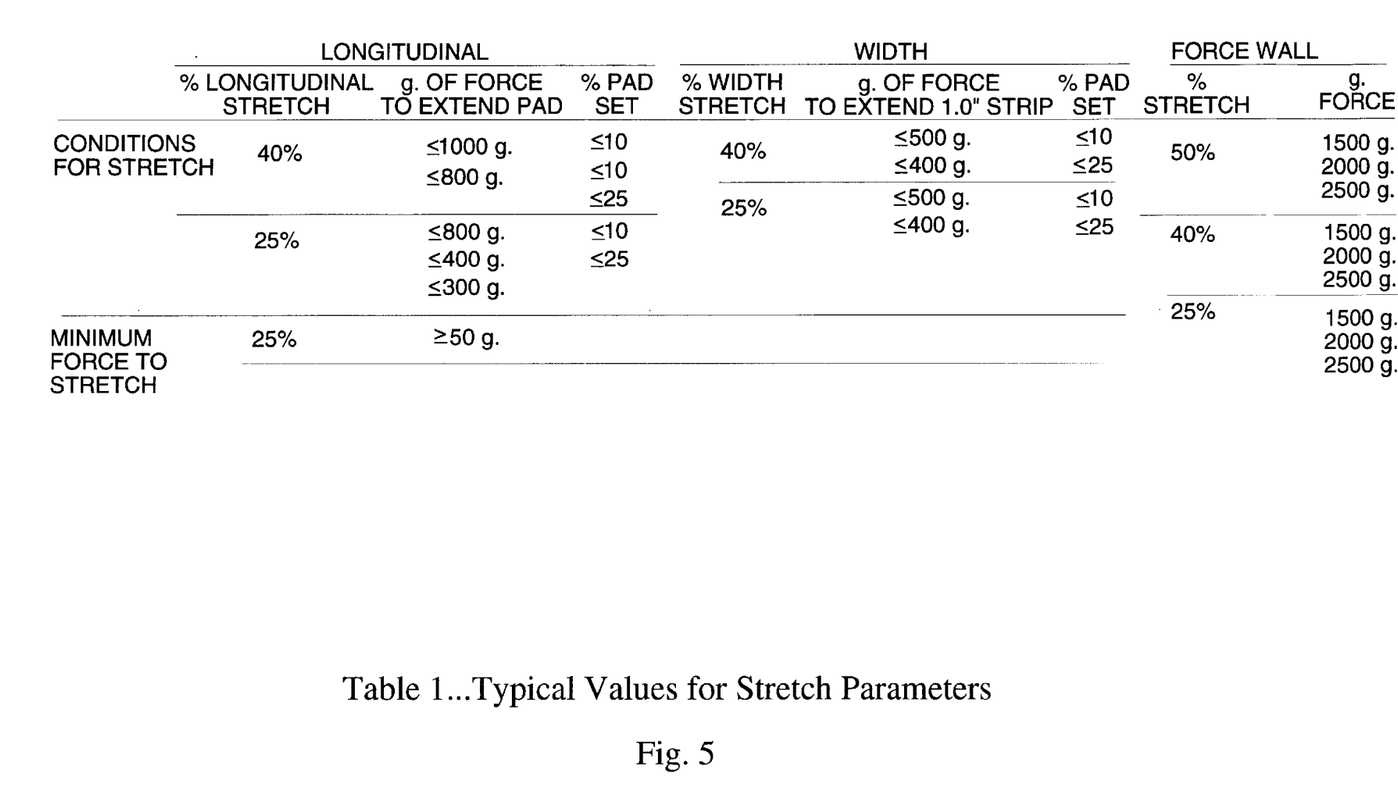
FIG. 5 is a table which shows preferred relationships between the magnitude of stretching forces applied to the sanitary napkin and the amount the sanitary napkin stretches in response to such forces.

The sanitary napkin is preferably extensible in the amounts described in PCT Publication Nos. WO 93/01785 and WO 93/01786. To summarize the same, the sanitary napkin is preferably capable of extending about 5% to less than about 50%, more preferably between about 10% and about 40%, and most preferably between about 25% and about 40% under the forces associated with wearing the sanitary napkin in a pair of panties. Preferably, the sanitary napkin is capable of such extension under forces of between about 50–100 grams and about 1,000–1,500 grams, more preferably under forces of between about 250 grams and about 800 grams. The absorbent structure can be extensible in the same amounts and under the same forces. FIG. 5 is a table which sets forth some additional ranges of forces for the extensibility of preferred absorbent articles. It is to be understood that all of the limits and ranges specified herein include all narrower ranges, limits, and amounts that are within the specified limits and ranges. As shown in FIG. 5, the sanitary napkin can also be provided with a "force wall" to prevent elongation past a certain amount without substantial increases in the amount of force applied to the sanitary napkin.

Figure 3:
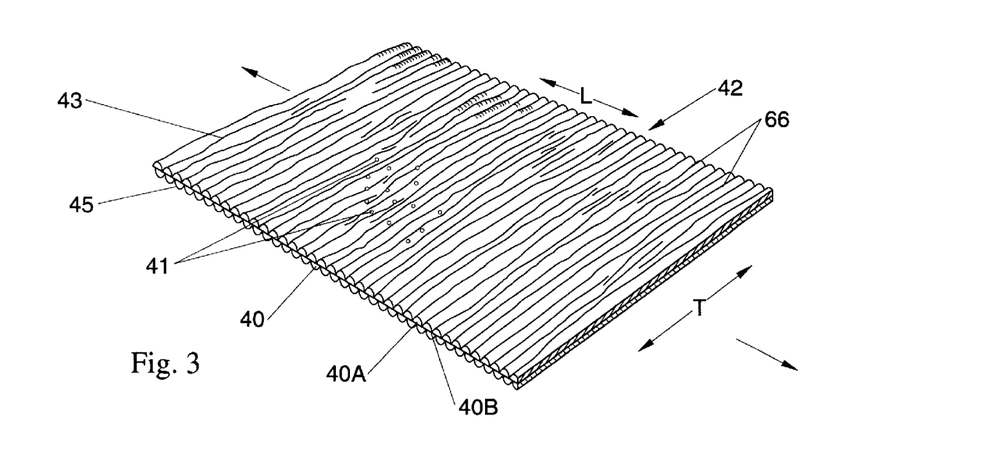
FIG. 3 is a perspective view of one embodiment of the stretchable absorbent structure of the present invention.

The individual components of the sanitary napkin 20 of the present invention will now be looked at in greater detail with reference to FIGS. 1–3.

The absorbent structure 42 of the present invention is shown in FIGS. 1 and 2 as underlying the topsheet 38. The absorbent structure shown is preferably elastically stretchable. (The absorbent structure may be referred to as the "stretchable absorbent structure" for brevity.) The stretchable absorbent structure 42 serves as the means for absorbing menses and other body fluids and as a backsheet that prevents exudates that have been absorbed from wetting articles that come in contact with the sanitary napkin such as the wearer's clothing and undergarments.

The stretchable absorbent structure 42 is a three-dimensional structure provided with an absorbent surface that has peaks and valleys therein. In the embodiment shown in FIGS. 1–3, the stretchable absorbent structure 42 comprises an absorbent component, such as a nonwoven web 43, that is laminated to a stretchable liquid impervious component, barrier film 40. The barrier film 40 provides the absorbent structure with its stretchability (and serves as a barrier to liquids). The nonwoven side of the stretchable absorbent structure 42 is preferably covered with a liquid pervious topsheet. In other embodiments such as in the case of the sanitary napkin shown in FIGS. 1 and 2, the stretchable absorbent structure is covered by a topsheet and a superabsorbent material containment layer and and then a topsheet.

The absorbent structure 42 is formed by laminating the nonwoven material 43 to the stretchable barrier film 40 when the barrier film is in an extended condition. The stretchable barrier film 40 is then relaxed. The laminate structure preferably has superabsorbent, hydrogel-forming material particles or fibers 41 disposed on or within the nonwoven component of the laminate. As shown in FIG. 3, when the absorbent structure 42 is in its unextended state, the surface of the absorbent structure is textured, and is preferably characterized by a plurality of rugosities 66.

The nonwoven component 43 of the absorbent structure can comprise a variety of types of nonwoven materials. Suitable nonwoven materials include, but are not limited to carded, spunbonded, wet-laid, meltblown, hydroentangled, combinations of the above, or the like materials. The nonwoven materials can comprise fibers made of natural or synthetic fibers. Suitable natural fibers include cellulosic and cotton fibers. Suitable synthetic fibers comprise polyolefinic materials, such as polyester, polypropylene, and bi-component fibers. The fibers comprising the nonwoven material preferably have a denier per fiber of between about 1 and about 30. The fibers comprising the nonwoven material can be of uniform or mixed material composition and/or denier. The nonwoven material preferably has a caliper of between about 0.7 mm and about 0.30 mm and a basis weight of between about 9 $g/m^2$ and about 25 $g/m^2$.

The fibers of the nonwoven material and the material itself can be provided with a surface treatment that may either be hydrophilic or hydrophobic. The nonwoven material can be rendered hydrophilic by corona discharge treating the same, by incorporating surfactant into the fibers, by spraying surfactant onto the fibers of the nonwoven material, or by other known methods. A suitable surfactant for spraying onto the nonwoven is Pegosperse 200 ML by Lonza, Inc., Williamsport, Pa.

In variations of the nonwoven material described above, the nonwoven material may comprise capillary channel fibers (i.e., fibers having intra-fiber capillary channels, especially on their exterior surfaces). Capillary channel fibers may be used to assist in the transportation of liquids (either per se, or in a particular direction). Suitable capillary channel fibers are described in U.S. Pat. No. 5,200,248 issued to Thompson, et al. on Apr. 6, 1993. In other variations, when the nonwoven component is comprised of synthetic fibers, small amounts of natural fibers including cellulose fibers, such as Northern softwood Kraft fibers, or cotton fibers can be included in the nonwoven material to assist in the absorption and transportation of liquids.

The superabsorbent material comprises hydrogel-forming polymeric gelling agents which may also be referred to as "absorbent gelling materials". Polymeric gelling agents are those materials which, upon contact with liquids such as water or other body liquids, imbibe such liquids and thereby form hydrogels. In this manner, liquids discharged into the stretchable absorbent structure 42 can be acquired and held by the polymeric gelling agent, thereby providing the articles herein with enhanced absorbent capacity and/or improved liquid retention performance. The polymeric gelling agent which is employed in the absorbent structure 42 will generally comprise particles 41 of a substantially water-insoluble, slightly cross-linked, partially neutralized, hydrogel-forming polymer material. The polymeric gelling agent used in the present invention can be in any form, including, but not limited to, in the form of pellets, flakes, or fibers.

The superabsorbent material, if in the form of particles (as opposed to fibers), are preferably affixed (i.e., adhered) to the nonwoven material. This can be done in a number of different ways before or after the nonwoven component is bonded to the barrier film. These different ways of adhering the superabsorbent material particles to the nonwoven material include, but are not limited to the following.

The superabsorbent material particles can be adhered to the nonwoven material by the use of moisture (e.g., steam, water mist, or by pre-wetting the superabsorbent material particles before they are placed on the nonwoven material.

The superabsorbent material particles can be adhered to the nonwoven material by the use of conventional adhesives, including, hot melt adhesives, water based adhesives, and other types of adhesives known in the art. The adhesives can be applied in any type of suitable configuration known in the art, including, but not limited to sprays, spirals, and the like. The superabsorbent material particles can also be adhered to the nonwoven material by using a chemical (preferably, a non-toxic chemical) such as glycerol or glycerin, or other chemical to swell the superabsorbent material particles and make the surfaces of the particles tacky so they adhere to the fibers of the nonwoven material.

If the superabsorbent material is in the form of fibers, the fibrous superabsorbent material is preferably combined with any other fibrous material used to make the nonwoven and formed integrally into the nonwoven component. Alternatively, the nonwoven material can be comprised entirely of the fibers of superabsorbent material.

The longitudinal side edges 42C and end edges 42D of the absorbent structure 42 may be sealed to prevent the wicking and expulsion of liquid or liquid-containing superabsorbent material from the napkin when it is worn. The edges of the absorbent structure 42 ,ay, for example, be wrapped or covered by a tissue layer. Alternatively, the edges of the tissue may be folded, or otherwise manipulated to prevent the wicking and expulsion of liquid or liquid-containing superabsorbent material particles 41 from the absorbent structure 42. In other alternate embodiments, the longitudinal and end edges 22 and 24 of the sanitary napkin 20 may be sealed for this purpose. All permanent seals around the perimeter of the sanitary napkin 20 should not break upon lengthening (i.e., any seal is intended to remain for the duration of the use of the sanitary napkin.)

The barrier 40 is impervious to liquids and, thus, prevents body fluids from soiling the clothing of the user. The barrier 40 may be manufactured from a range of extensible, preferably stretchable, more preferably elastically extensible, liquid impervious materials.

In the preferred embodiment shown, the barrier 40 comprises a film, barrier film 40. Suitable films include an extensible, preferably elastically extensible film such as a film made in accordance with U.S. Pat. No. 4,476,180 issued to Wnuk on Apr. 16, 1991. One such film is Exxon elastomeric film EX-500 (formerly EXX-7) made by Exxon Chemical Company of Lake Zurich, Ill. Another preferred film is an extensible adhesive film Formula #198-338 manufactured by the Findley Adhesives Company of Wauwatosa, Wis. The Findley adhesive film is a fluid impervious film capable of extending 200–300%. It is preferred because it is also elastically extensible.

The absorbent structure 42 is assembled by stretching the barrier film 40 at least part of the way toward its completely stretched condition, and laminating the barrier film 40 and the nonwoven together 43. The barrier film 40 is preferably stretched about 150% of its unstretched length (that is, 1.5 times its unstretched length). The barrier film 40 and nonwoven 43 may be laminated in any suitable manner which provides the absorbent structure formed thereby with stretchability and a three dimensional surface. Preferably, the barrier film 40 and the nonwoven 43 are laminated by applying adhesive in the form of parallel beads oriented in the longitudinal direction of the finished absorbent structure 42. When the tension is removed from the film, the barrier film 40 will retract forming a plurality of transverse rugosities 66. This will provide the absorbent structure 42 with longitudinal extensibility.

The absorbent structure can also be provided with multi-direction extensibility (or stretchability). This can be done in any suitable manner. For example, the absorbent structure can be provided with multi-direction stretchability by simultaneously stretching the barrier film in more than one direction during lamination. In other alternative embodiments, a mechanical operation such as ringrolling or creping can be performed on the absorbent structure following lamination. Alternatively, the nonwoven material can be bonded to the barrier film using bond patterns that provide multi-directional stretch. For example, the barrier film can be stretched and the adhesive can be applied in a spot or diamond pattern and the nonwoven applied, to provide multi-directional stretch.

Many alternative embodiments of the absorbent structure of the present invention are possible. For example, as shown in FIG. 3, another layer of nonwoven material 45 can be secured to the other side of the barrier film 40. In other variations, the amount that he barrier film is stretched and the glue pattern can be varied to vary the size and shape of the rugosities (e.g., more stretching and larger spaces between the glue bonds will yield larger rugosities). In alternative embodiments, the nonwoven material layer can be folded into a nonwoven sandwich and then laminated onto a pre-stretched barrier layer.

The absorbent structure can also be provided with density gradients, capillary gradients, superabsorbent gradients, lower density and lower average basis weight acquisition zones, and the like. For example, regions of high density can be imparted to the absorbent structure by compression to enhance liquid acquisition, storage, and distribution.

The absorbent component of the absorbent structure 42 is also not limited to the particular superabsorbent material-containing nonwoven material described above. The absorbent component can comprise any material used in the art for such purpose. Non-limiting examples include natural materials such as comminuted wood pulp which is generally referred to as airfelt, creped cellulose wadding, modified cross-linked cellulose fibers (such a those described in U.S. Pat. No. 5,217,445 issued to Young, et al. on Jun. 8, 1993), capillary channel fibers, absorbent foams, absorbent sponges, synthetic staple fibers, polymeric fibers, peat moss, or any equivalent material or combinations of materials.

In embodiment in which an extensible adhesive film is used as the barrier film, the film can be used "as is" in the sanitary napkin 20. For example, one side of the adhesive film (the designated 40A in FIG. 3) can be adhered to the nonwoven material 43. The other side 40B, comprising the garment-facing side of the barrier film 40, may be used as a panty fastening adhesive. Alternatively, the side of the adhesive film that forms the garment-facing side 40B may have its adhesive surface at least partially covered (or "blocked" to eliminate its adhesive characteristics). The adhesive body-facing side 40A of the barrier film can also be completely or partially blocked.

The exposed adhesive can be blocked in a number of suitable ways. These include, but are not limited to attaching a layer of nonadhesive material to cover the exposed adhesive, and brushing or sprinkling a powdered material such as talcum powder or corn starch on at least part of the exposed adhesive. The partial blocking of the exposed adhesive on the garment-facing side 40B of the barrier film 40 can be used with the remaining exposed adhesive to create particular panty fastening adhesive patterns.

In still other embodiments, an adhesive film can be created with one side that has adhesive tack, and one side without tack. One suitable adhesive film having these characteristics is a composite structure comprising a nonwoven elastomeric film with a low modulus pressure sensitive adhesive, such as adhesive film Formula #198-338 which is available with a blocking film such as film Formula H2301 from the Findley Adhesives Company. Such materials are further described (and used for other purposes) in U.S. Pat. No. 5,032,120 issued to Freeland, et al. on Jul. 16, 1991, and U.S. Pat. No. 5,037,416 issued to Allen, et al. on Aug. 6, 1991.

The absorbent structure 42 of the present invention provides a large number of advantages. The elimination of many tissue layers and folding operations substantially reduces the cost of making the absorbent structure and allows the absorbent article containing the same to be made very thin and flexible.

The rugosities associated with the nonwoven material provide more voids and large voids (that is, a higher void volume) than homogeneous web structures or laminate structures. The voids are useful for providing areas for the superabsorbent material particles to swell into after they absorb liquids. This is believed to provide the absorbent structure with greater liquid holding capacity for the same amount of superabsorbent material in comparison to laminate structures which have superabsorbent material between the layers of the laminate.

The rugosities are also believed to permit the use of higher concentrations of superabsorbent material per given area (e.g., per $cm^2$). Higher concentrations of superabsorbent materials can also be effectively added to critical regions of the absorbent article because there is a z-directional distribution of the superabsorbent material in a structure with a high void volume. (The process of depositing the superabsorbent material on a structure with rugosities, or on a planar structure that is later provided with rugosities will create a z-directional distribution of superabsorbent material.) In addition, the absorbent structure can be provided with an excess concentration of superabsorbent material when the absorbent structure is in a relaxed state, which will produce a superabsorbent material concentration within a desired target level when the absorbent structure is extended.

The surface rugosities also provide a "surge" volume for temporarily holding gushes of free liquids until they are absorbed by the superabsorbent material particles. The surface rugosities also provide a softer-feeling, more resilient ("cushy") structure for improved wearing comfort. In addition, previous attempts to place particulate suberabsorbent material directly on a thin barrier of the type used in the present invention resulted in pin holes being formed into the barrier, particularly when pressure was applied on the absorbent article during manufacture or wear. This would result in liquid leaking through the barrier or the superabsorbent material particles from escaping through the barrier both during manufacture and in use. The nonwoven material used in the absorbent structure reduces or eliminates this problem by providing a cushion that prevents such pin holes from forming when pressure is applied to the absorbent structure.

The topsheet 38 comprises a liquid pervious component that is in close proximity to the skin of the user when the sanitary napkin 20 is in use. The topsheet 38 is preferably as compliant, soft feeling, and non-irritating to the user's skin as possible. The topsheet 38 should further exhibit good strikethrough and a reduced tendency to rewet, permitting bodily discharges to rapidly penetrate it and flow toward the absorbent structure 42, but not allowing such discharges to flow back through the topsheet 38 to the skin of the wearer.

The topsheet 38 has two sides (or faces or surfaces), including a body-facing side 38A and a garment-facing side 38B. The body-facing side 38A of the topsheet 38 generally forms at least a portion of the body-contacting surface ("body surface") 20A of the sanitary napkin 20. The topsheet 38 has two longitudinal edges 38C and two end edges 38D. (A similar numbering system applies to the other components of the sanitary napkin. That is, the side of the component facing the wearer's body can be designated by the number of the component and a reference letter "A". The side facing the wearer's undergarments can be designated by the number of the component and the letter "B". The side and end edges can be designated by the number of the component and the reference letters "C" and "D", respectively.)

A suitable topsheet 38 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven material can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. When the topsheet 38 comprises a nonwoven web, the web may be spunbonded, carded, wet-laid, meltblown, hydroentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991.

The topsheet 38 can be made extensible by performing a mechanical operation, such as pleating, corrugating, or ring rolling on the topsheet material to provide folds in the topsheet that are able to open when the topsheet is stretched. Such a process can be performed on many of the topsheet materials described above. In one preferred embodiment of the present invention, the topsheet 38 is made in accordance with U.S. Pat. No. 4,463,045 and ring rolled to provide it with a degree of longitudinal extensibility. Such a topsheet is described in U.S. patent application Ser. No. 07/936,195 entitled "Polymeric Web Having Deformed Sections Which Provide a Substantially Increased Elasticity To The Web", filed in the name of John J. Curro, et al. on Aug. 25, 1992.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B Buell et al. on Feb. 28, 1991, and U.S. patent application Ser. No. 07/662,543 filed by Gerald M. Weber et al. on Feb. 28, 1991.

The fold lines in the corrugations of a ring rolled topsheet preferably run in the transverse direction so the topsheet is longitudinally extensible. In other embodiments, the fold lines could run in the longitudinal direction, both directions, and/or other directions. The topsheet 38 will be extensible in directions perpendicular to the fold lines.

In a preferred embodiment, the topsheet 38 is hydrophilic so that liquids will transfer through the topsheet 38 faster. This will diminish the likelihood that body exudates will flow off the topsheet rather than being absorbed into the absorbent structure. The topsheet can be rendered hydrophilic by treating it with surfactants. Suitable methods of applying surfactants are described in U.S. Pat. Nos. 4,950,264 and 5,009,653 issued to Osborn.

In addition, in preferred embodiments, the inner surface 38 of topsheet 38 is secured in contacting relation with an underlying absorbent layer. This contacting relationship results in liquid penetrating topsheet 38 faster. The topsheet 38 may be kept in a contacting relationship with an underlying layer by bonding the topsheet to the underlying layer. However, it is not absolutely necessary to bond the face of the topsheet 38 to the face of the underlying layer. The topsheet 38 can be maintained in contact with an underlying absorbent component by applying adhesives between the topsheet and the underlying component, by entangling the fibers of the underlying layer with the topsheet, by fusing the topsheet 38 to an underlying absorbent layer by a plurality of discrete individual fusion bonds, or by any means known in the art.

The superabsorbent material containment component (or "containment layer") 46 is positioned between the topsheet 38 and the absorbent structure 42. The containment layer 46 is used to prevent any loose superabsorbent material particles 41 in the nonwoven component 43 from passing through the topsheet 38 (and out of the sanitary napkin) either during manufacture or wear.

The containment layer 46 may comprise any material that is suitable for the above purpose which does not interfere with the transportation of liquids that pass through the topsheet into the absorbent structure. Suitable containment layers are described in PCT Publication Nos. WO 93/01785 and WO 93/10786. Other suitable materials for the containment layer comprise creped tissue paper, and meltblown composites, such as product number 8144-102 obtained from Fiberweb North America of Simponsvile, S.C. The containment layer 46 may also comprise any of the material specified as being suitable for use as the topsheet if fibrous superabsorbent material is used. Such materials are believed to be particularly useful in prevent in the superabsorbent material from "bleeding" through to the body facing surface of the produce, where fibrous superabsorbent material is used.

The containment layer 46 can be made extensible by performing a mechanical operation, such as pleating, corrugating, creping, or ringrolling the material used for the containment layer. Preferably, the containment layer 46 is provided with extensibility by making the same from tissue paper having between 20% and 200% stretch (i.e., capable of extending between about 1.2 to 3.0 times its original length). The corrugations should be perpendicular to the direction of desired stretch. Such tissue sheets can be made by a number of processes. The tissue paper may in one embodiment, be conventionally creped tissue. For example, the tissue paper may be a BOUNTY tissue that has retained substantial crepe after removal from the Yankee dryer in the papermaking process. A process for making such a tissue is described in U.S. Pat. No. 5,098,522 issued to Smurkoksi, et al. on Mar. 24, 1992.

The components of the sanitary napkin described above (the topsheet, the containment layer, and the absorbent structure) an be secured together in any suitable manner that allows the sanitary napkin 20 to extend. In the preferred embodiment shown in FIG. 1, the components of the sanitary napkin 20 are sized so that the edges of the topsheet 38 and barrier film 40 extend outward beyond the edges of the nonwoven component 43 of the absorbent structure 42. The topsheet 38 and the containment layer 46 are placed on top of the absorbent structure 42. The portions of the edges of the topsheet 38 that extend outward beyond those of the nonwoven 43 are secured to those of the barrier film 40. As shown in FIG. 1, the topsheet 38 is preferably secured to barrier film 40 along a seam 90. Seam 90 is preferably liquid impervious. The seam 90 can be formed by any means commonly used in the art for this purpose such as by gluing, crimping, or heat-sealing.

The above is a preferred embodiment for ease of construction. (Other means of uniting the various components can be used.) For instance, the absorbent structure of the present invention can also be used in so-called "tube" products. In these products, a liquid pervious cover material (such as topsheet material) can be wrapped completely around the absorbent structure and secured to the absorbent structure.

FIG. 2 shows that the garment surface 20B of the sanitary napkin may be provided with a fastener, such as pressure sensitive adhesive 50, to secure the sanitary napkin 20 to the crotch of a panty. The adhesive can be applied in several suitable configurations. Preferred adhesive patterns are described in PCT Publication Nos. WO 93/01785 and 93/01786. The adhesive fastener 50 can be extensible, inextensible, or a combination of extensible and inextensible adhesives.

If the adhesive is extensible, it preferably extends approximately the same amounts as the sanitary napkin as set forth in Table 1. Suitable extensible adhesives include extensible adhesives, per se, and extensible adhesive/barrier film combinations. Any extensible adhesives known in the art can be used. Suitable extensible adhesive/barrier film combinations include, but are not limited to non-extensible adhesive used on an extensible barrier film material; elastically stretchable adhesive films such as Findley adhesive 198-338; or spray adhesives such as 3M adhesive 1442 on a low modulus elastic film.

Suitable inextensible adhesives may be those adhesives specified as 0.6 mil pass available from Century Adhesive as product number A305-4, or from Anchor Continental, Inc., 3 Sigma Division, of Covington, Ohio, and Fuller H-2238ZP manufactured by the H.B. Fuller Co. Suitable inextensible adhesive fasteners are described in greater detail in U.S. Pat. No. 4,917,697.

The adhesive fastener 50 is preferably covered with a release liner (or cover strip) 52. Any commercially available release liner can be used. In one preferred embodiment, the release liner can be replaced by a wrapper that provides both an individually packaged sanitary napkin and a container for disposing the sanitary napkin after use, such as is described in U.S. Pat. No. 4,556,146 issued to Swanson, et al. on Dec. 3, 1985.

The fasteners have been initially described in terms of adhesives for simplicity of description. The types of fasteners are not limited to adhesives, however. Preferred fasteners include but are not limited to adhesive fastening means, such as pressure sensitive adhesives, mechanical fasteners and combinations of adhesives and mechanical fasteners.

The following Example further illustrates the practice of the present invention. The following Example, however, is not intended to limit the scope of the absorbent articles encompassed herein.

EXAMPLE

The topsheet 38 is made in accordance with U.S. Pat. No. 4,463,045 and ring rolled to provide it with extensibility. The containment layer is a single ply of creped BOUNTY tissue. The nonwoven layers are 11 g/m$^2$ polypropylene manufactured by Scott under the product code 2022CA. The barrier film is 1.5 mil caliper film known as EXX-7A obtained from Exxon Chemical Company.

The stretchable absorbent structure is initially prepared by stretching the barrier film to about 1.5 times its original length and extruding Findley H-2031 glue onto both sides of the film. The glue is applied in the form of continuous filaments approximately 1 mm wide which are separated by approximately ⅜" (9.5 mm). The Scott nonwoven is laminated onto both sides of the film, forming a trilaminate. The stretchable absorbent structure is then cut into the desired shape for the sanitary napkin.

The spiral pattern of Findley 2031 adhesive is applied to one side of the stretchable absorbent structure and 1.0 gram of Nalco 1180 absorbent gelling material (AGM) is distributed over the surface of this side of the stretchable absorbent structure. The side of the absorbent structure with the superabsorbent material is covered with a single ply creped tissue (% elongation to break is greater than or equal to 200%). A layer of Findley 2031 adhesive is applied in a spiral pattern to the outwardly facing side of the tissue. Hot melt Findley adhesive 990 is applied along the edges of the barrier and the ring rolled topsheet material is applied to the partially assembled product so that the product will stretch in the longitudinal direction. The assembly is then pressed together. Fuller extensible adhesive 2254 is applied to the back of the barrier as a panty fastening adhesive (PFA). One skilled in the art can easily re-orient the materials to produce lateral stretch.

While a preferred sanitary napkin embodiment has been described, numerous other sanitary napkin embodiments are disclosed in the literature. These could be provided with a stretchable absorbent structure. Some of such sanitary napkins are described in U.S. patent application Ser. No. 07/944,764 filed in the name of Cree, et al. on Sep. 14, 1992, and in U.S. Pat. Nos. 5,009,653 and 4,950,264, issued to Osborn on Apr. 23, 1991 and Aug. 21, 1990, respectively.

The terms "panty liner" or "pantiliner" refer to absorbent articles that are less bulky and less absorbent than sanitary napkins which are often worn by women between their menstrual periods or in combination with a tampon. An example of an absorbent article in the form of a pantiliner is disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Some examples of incontinence articles that can be provided with a stretchable absorbent structure are disclosed in U.S. Pat. No. 4,253,461 issued to Strikland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991 (PCT Publication Nos. WO 92/11830 and WO 92/11831, both published Jul. 23, 1992).

The focus of the present invention is on absorbent articles that are intended to be worn in the crotch region of the wearer's undergarments. However, the stretchable absorbent structure of the present invention could also be used in absorbent articles such as diapers. Diapers are absorbent articles worn by infants and incontinent persons that are fastened about the waist of the wearer. Suitable diapers that can be provided wit ha stretchable absorbent structure are disclosed in U.S. Pat. No. 3,860,003 issued to Buell on Jan. 14, 1975, and U.S. Pat. No. 5,151,092 issued to Buell, et al. on Sep. 29, 1992.

The disclosures of all patents, patent application (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An extensible absorbent article for wearing in a wearer's undergarment, and being capable of extending with said undergarment, said extensible absorbent article comprising:

an extensible liquid pervious topsheet;

an elastically stretchable liquid impervious component joined to said topsheet, said liquid impervious component having two opposed faces, a relaxed condition, and a stretched condition;

an absorbent nonwoven component having two opposed generally planar faces prior to inclusion in said absorbent article, said nonwoven component being positioned between said topsheet and said liquid impervious component and bonded in a face-to-face relationship to said liquid impervious component when said liquid impervious component is stretched at least partially to its stretched condition;

wherein rugosities are formed in portions of said nonwoven component when said liquid impervious component is relaxed so that said nonwoven component can be extended by the straightening of said rugosities when said absorbent article is extended, and said impervious component serves as a liquid impervious barrier for he absorbent article; and a fastener on said liquid impervious component for fastening said extensible absorbent article to a wearer's undergarment.

2. An extensible absorbent article for wearing in a wearer's undergarment, and being capable of extending with said undergarment, said extensible absorbent article comprising:

an extensible liquid pervious topsheet;

an elastically stretchable liquid impervious component joined to said topsheet, said liquid impervious component having two opposed faces, a relaxed condition, and a stretched condition;

an absorbent nonwoven component having two opposed generally planar faces prior to inclusion in said absorbent article, said nonwoven component being positioned between said topsheet and said liquid impervious component and bonded in a face-to-face relationship to said liquid impervious component when said liquid impervious component is stretched at least partially to its stretched condition;

wherein rugosities are formed in portions of said nonwoven component when said liquid impervious component is relaxed so that said nonwoven component can be extended by the straightening of said rugosities when said absorbent article is extended, and said impervious component serves as a liquid impervious barrier for the absorbent article wherein said absorbent article extends between about 5% and less than about 50% under forces of between about 50 grams and about 1,500 grams.

3. The absorbent article of claim 1 wherein said nonwoven component comprises at least some synthetic fibers.

4. The absorbent article of claim 1 wherein said nonwoven component comprises at least some natural fibers.

5. The absorbent article of claim 1 further comprising superabsorbent, hydrogel-forming material on said nonwoven component.

6. The absorbent article of claim 5 wherein said superabsorbent, hydrogel-forming material is particulate.

7. The absorbent article of claim 5 wherein said superabsorbent, hydrogel-forming material is bonded to said nonwoven component by moisture bonds.

8. The absorbent article of claim 6 wherein said superabsorbent, hydrogel-forming material is bonded to said nonwoven component by adhesive.

9. The absorbent article of claim 8 further comprising a superabsorbent material containment layer positioned between said topsheet and said nonwoven component.

10. The absorbent article of claim 1 further comprising superabsorbent, hydrogel-forming material in said nonwoven component.

11. The absorbent article of claim 10 wherein said superabsorbent, hydrogel-forming material is fibrous.

12. The absorbent article of claim 11 wherein said fibrous superabsorbent material is an integral part of the nonwoven component.

13. An extensible absorbent article for wearing in a wearer's undergarment, and being capable of extending with said undergarment, said extensible absorbent article comprising:

an extensible liquid pervious topsheet;

a stretchable absorbent structure joined to said topsheet, said absorbent structure comprising:

a stretchable liquid impervious liquid barrier layer, said liquid barrier layer having two opposed faces, a relaxed condition, and a stretched condition;

a fibrous nonwoven absorbent component comprising a plurality of fibers, said nonwoven component having two opposed, generally planar faces prior to inclusion in said absorbent article, said nonwoven component being positioned between said barrier layer and said topsheet and being bonded in a face-to-face relationship to said barrier layer when said barrier layer is stretched at least partially to its stretched condition, wherein rugosities are formed in portions of said nonwoven component when said barrier layer is relaxed so that said nonwoven component can be extended by the straightening of said rugosities when said absorbent article is extended; and superabsorbent, hydrogel-forming material affixed to the fibers of said nonwoven component;

a liquid pervious superabsorbent material containment layer positioned between said absorbent structure and said topsheet;

wherein said absorbent article is capable of stretching between about 5% and less than about 50% under forces of between about 50 grams and about 1,500 grams force.

\* \* \* \* \*